(12) United States Patent
Patel et al.

(10) Patent No.: US 9,517,465 B2
(45) Date of Patent: Dec. 13, 2016

(54) LATERAL CAVITY ACOUSTIC TRANSDUCER BASED MICROFLUIDIC SWITCH

(75) Inventors: Maulik V. Patel, La Crescenta, CA (US); Armando R. Tovar, San Diego, CA (US); Abraham P. Lee, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1103 days.

(21) Appl. No.: 13/613,623

(22) Filed: Sep. 13, 2012

(65) Prior Publication Data

US 2014/0011291 A1    Jan. 9, 2014

Related U.S. Application Data

(60) Provisional application No. 61/534,327, filed on Sep. 13, 2011.

(51) Int. Cl.
*G01N 15/14* (2006.01)
*B01L 3/00* (2006.01)
*G01N 15/00* (2006.01)

(52) U.S. Cl.
CPC .... *B01L 3/502761* (2013.01); *B01L 3/502738* (2013.01); *G01N 15/1484* (2013.01); *B01L 2200/0636* (2013.01); *B01L 2200/0652* (2013.01); *B01L 2300/0816* (2013.01); *B01L 2400/0622* (2013.01); *G01N 2015/0053* (2013.01); *G01N 2015/149* (2013.01); *Y10T 436/2575* (2015.01)

(58) Field of Classification Search
None
See application file for complete search history.

(56) References Cited

U.S. PATENT DOCUMENTS 7,157,274 B2    1/2007  Bohm et al.
2012/0078531 A1  3/2012  Lo et al.

OTHER PUBLICATIONS

Tovar, A. et al. "Acoustic cavity transducers for the manipulation of cells and biomolecules," Proc. SPIE 7574, Nanocale Imaging, Sensing, and Actuation for Biomedical Applications VII, 757402, Feb. 12, 2010.*

(Continued)

*Primary Examiner* — Yelena G Gakh
*Assistant Examiner* — Michelle Adams
(74) *Attorney, Agent, or Firm* — Vista IP Law Group LLP

(57) ABSTRACT

A microfluidic switching device that includes an upstream microfluidic channel configured to contain a liquid having particles therein and a plurality of outlet channels coupled to the upstream microfluidic channel at a junction. A dead-end side channel or LCAT is oriented generally perpendicular to the upstream microfluidic channel and coupled to the upstream microfluidic channel at the junction, the dead-end side channel having a gas contained therein. The device includes a transducer configured to apply an external source of acoustic energy. Actuation of the transducer effectuates symmetrical oscillation of a gas/liquid boundary at the junction. Preferably, the junction comprises a bifurcation with two outlets. Further, the LCAT has a leading edge and a trailing edge and wherein the trailing edge of the LCAT is substantially aligned with the bifurcation.

9 Claims, 8 Drawing Sheets

(56) References Cited

OTHER PUBLICATIONS

Tovar, A. R. "Enabling microfluidic diagnostic devices using lateral cavity acoustic transducers for on-chip pumping," Dissertation, University of California, Irvine, Jun. 2010.*
Ahmed, Daniel et al., A fast microfluidic mixer based on acoustically driven sidewall-trapped microbubbles, Microfluid Nanofluid (2009) 7:727-731.
Baret, Jean-Christopher et al., Fluorescene-activated droplet sorting (FADS): efficient microfluidic cell sorting based on enzymatic activity, Lab Chip, Sep. 2009, 1850-1858.
Chen, Chun H. et al., Microfluidic cell sorter with integrated piezoelectric actuator, Biomed Microdevices (2009) 11:1223-1231.
Chung, Sang Kug et al., On-chip manipulation of objects using mobile oscillating bubbles, J. Micromech, Microeng. 18 (2008) 15024 (12pp).
Cho, Sung Hwan et al., Human mammalian cell sorting using a highly integrated micro-fabricated fluorescene-activated cell sorter (uFACS), Lab Chip, Oct. 2010, 1567-1573.
Duffy, David C. et al., Rapid prototyping of microfluidic switches in poly(dimethyl siloxane) and their actuation by electro-osmotic flow, J. Micromech. Microeng. 9 (1999) 211-217. Printed in the UK.
Marmottant, Philippe et al., A bubble-driven microfluidic transport element for bioengineering, PNAS, Jun. 29, 2004, vol. 101, No. 26, 9523-9527.
Wang, Cheng et al., Efficient manipulation of microparticles in bubble streaming flows, Biomicrofluidics 6, 012801 (2012).
Wang, Cheng et al., Size-sensitive sorting of microparticles through control of flow geometry, Appl. Phys. Lett. 99, 034101 (2011).

* cited by examiner

LATERAL CAVITY ACOUSTIC TRANSDUCER BASED MICROFLUIDIC SWITCH

RELATED APPLICATION

This application claims priority to U.S. Provisional Patent Application No. 61/534,327, filed on Sep. 13, 2011, which is hereby incorporated by reference in its entirety. Priority is claimed pursuant to 35 U.S.C. §119.

STATEMENT REGARDING FEDERALLY SPONSORED RESEARCH OR DEVELOPMENT

This invention was made with Government support under Grant No. HR0011-06-1-0050, awarded by the Department of Defense. The Government has certain rights in this invention.

FIELD OF THE INVENTION

The field of the invention generally relates to microfluidic devices and more particularly to microfluidic devices with switching capability.

BACKGROUND

The rapid growth of microfluidic technologies in the last several decades has led to the development of various degrees of micro total analysis systems. Specifically, the application of microfluidic technologies to the field of cell biology have enabled the development of integrated "lab on a chip" systems that are capable of integrating multiple laboratory steps on to a single device. An important cell manipulation process that needs to be integrated into a "lab on a chip" system is the ability to switch cells of interest to multiple downstream processes for further analysis.

Multiple microfluidic switches for particles and cells have been developed including electro-osmotic flow (EOF), dielectrophoresis, microfabricated valves, external valves and optical tweezers. These microfluidic switches were later utilized in integrated micro Fluorescence Activated Cell Sorting (µFACS) systems. However, many of the current microfluidic switches have several drawbacks such as low throughput, low cell recovery, complex off-chip optical tweezer or pneumatic valves setup and high voltages (kV).

Recently, there has been increasing interest in utilizing acoustically excited bubbles within microchannels as simple on-chip actuator systems for applications in pumping, mixing and trapping. Specifically, Lateral Cavity Acoustic Transducers (LCATs) are simple on-chip actuators that are easily fabricated and can be actuated using a battery operated portable electronics platform. LCATs are dead-end side channels that are in the same plane as the microchannels themselves requiring no additional fabrication steps other than those needed to produce the single layer device. When the device is filled with liquid, LCATs trap bubbles creating an air-liquid interface that can be excited using an external acoustic source such as a piezoelectric transducer.

Patel et al. demonstrated the potential application of LCATs for particle and cell sorting applications. See Patel et al., Thirteenth International Conference on Miniaturized Systems for Chemistry and Life Sciences November 1-5, µTAS, Jeju, Korea (2009). In the device disclosed in Patel et al., the LCAT is positioned upstream of the outlet junctions. This configuration produced instabilities in the air/liquid oscillations and required higher voltages in order to generate particular patterns of streaming.

SUMMARY

One embodiment includes a microfluidic switching device that includes an upstream microfluidic channel configured to contain a liquid having particles therein and a plurality of outlet channels coupled to the upstream microfluidic channel at a junction. A dead-end side channel or LCAT is oriented generally perpendicular to the upstream microfluidic channel and coupled to the upstream microfluidic channel at the junction, the dead-end side channel having a gas contained therein. The device includes a transducer configured to apply an external source of acoustic energy. Actuation of the transducer effectuates symmetrical oscillation of a gas/liquid boundary at the junction. Preferably, the junction comprises a bifurcation with two outlets. Further, the LCAT has a leading edge and a trailing edge and wherein the trailing edge of the LCAT is substantially aligned with the bifurcation.

Another embodiment includes a microfluidic switching device that has an upstream microfluidic channel configured to contain a liquid having particles therein, a plurality of at least three outlet channels coupled to the upstream microfluidic channel at a junction, and a dead-end side channel oriented at an angle to the upstream microfluidic channel and coupled to the upstream microfluidic channel at the junction, the dead-end side channel having a gas contained therein. The device further includes a transducer configured to apply an external source of acoustic energy. Actuation of the transducer effectuates symmetrical oscillation of a gas/liquid boundary at the junction. In this embodiment, the LCAT cavity (or multiple cavities) are angled with respect to the upstream microfluidic channel.

Still another embodiment includes a method of switching particles in a microfluidic device. The method includes providing a microfluidic device having an upstream microfluidic channel and a plurality of outlet channels coupled to the upstream microfluidic channel at a junction, the device having a dead-end side channel oriented generally perpendicular to the upstream microfluidic channel and coupled to the upstream microfluidic channel at the junction, the dead-end side channel having a gas contained therein. A liquid containing particles is then flowed through the upstream microfluidic channel and a transducer acoustically coupled to the microfluidic device is actuated, wherein actuation of the transducer effectuates symmetrical oscillation of a gas/liquid boundary at the junction, wherein at least some of the particles are switched to one of the plurality of outlets.

DETAILED DESCRIPTION OF THE ILLUSTRATED EMBODIMENTS

Figure 1A:
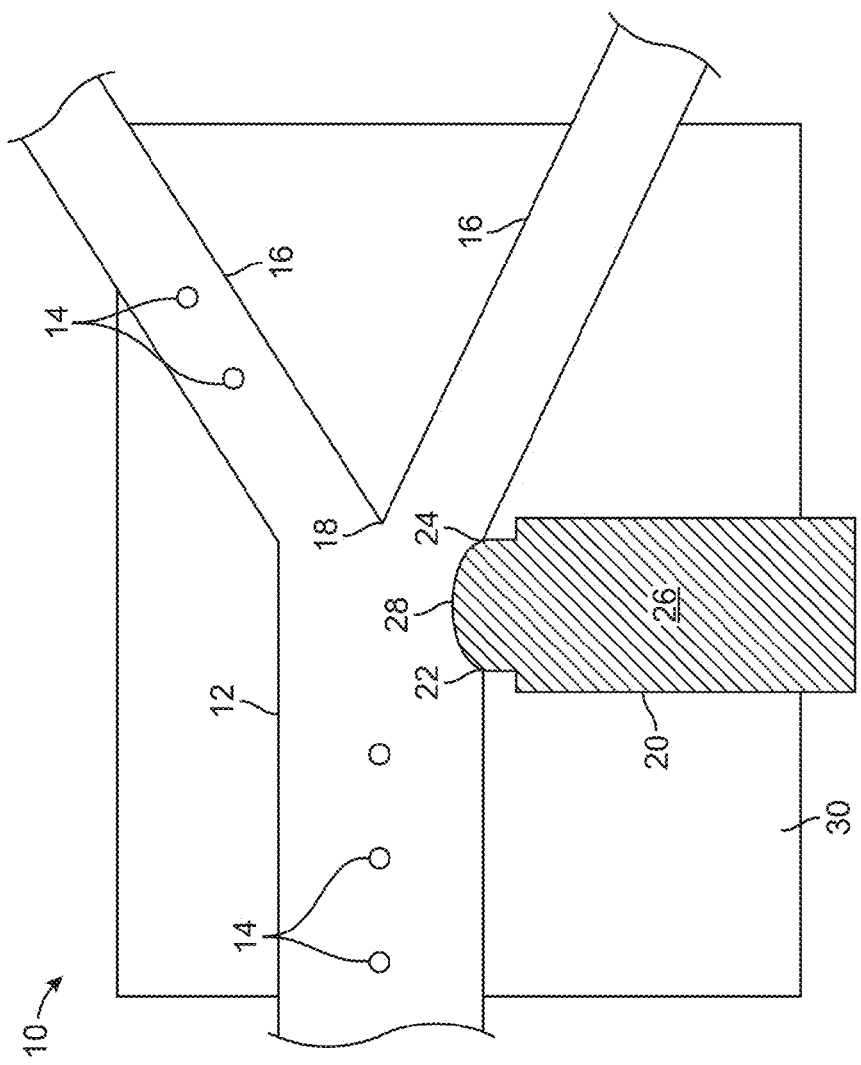
FIG. 1A schematically illustrates one embodiment of a microfluidic switching device.

FIG. 1A illustrates a view of a portion of a microfluidic switching device 10. The microfluidic switching device 10 may be referred to as a Lateral Cavity Acoustic Transducer (LCAT) device 10 because of the use of a lateral dead-end side channel that contains a gas therein that oscillates in response to applied acoustic energy. Illustrated in FIG. 1A is an upstream microfluidic channel 12 that is configured to contain a liquid therein that contains particles 14. Particles 14 may include objects such as beads or the like as well as biological based objects such as cells. As explained in more detail below, in one preferred aspect of the invention, the microfluidic switching device 10 may switch live cells. Still referring to FIG. 1A, the upstream microfluidic channel 12 is coupled to a plurality of outlet channels 16 at a junction 18. The junction 18 illustrated in FIG. 1A is a bifurcation meaning that there are two outlet channels 16. The microfluidic switching device 10 includes a dead-end side channel 20 that is fluidically coupled to the upstream microfluidic channel 12 at the junction 18. As seen in FIG. 1A, the dead-end side channel 20 is oriented generally perpendicular to the long axis of the upstream microfluidic channel 12. The dead-end side channel 20 includes leading edge 22 and a trailing edge 24. The width between the leading edge 22 and the trailing edge 24 may vary. In some embodiments it is generally less than about 100 μm (e.g., 60 μm) although larger widths could also be used. Generally, smaller widths of the dead-end side channel 20 results in a more stable design. Additionally, smaller LCAT cavity widths decreases the inter-particle distance required to switch every other particle if desired.

As seen in FIG. 1A, the dead-end side channel 20 contains a gas 26 therein. The gas 26 may include air although other gases may be used. A gas/liquid interface 28 is created that, as explained below, undergoes oscillation in response to acoustic coupling from a separate transducer 30. As seen in FIG. 1A, particles 14 are being switched from the upstream microfluidic channel 12 to the upper outlet channel 16.

Figure 1B:
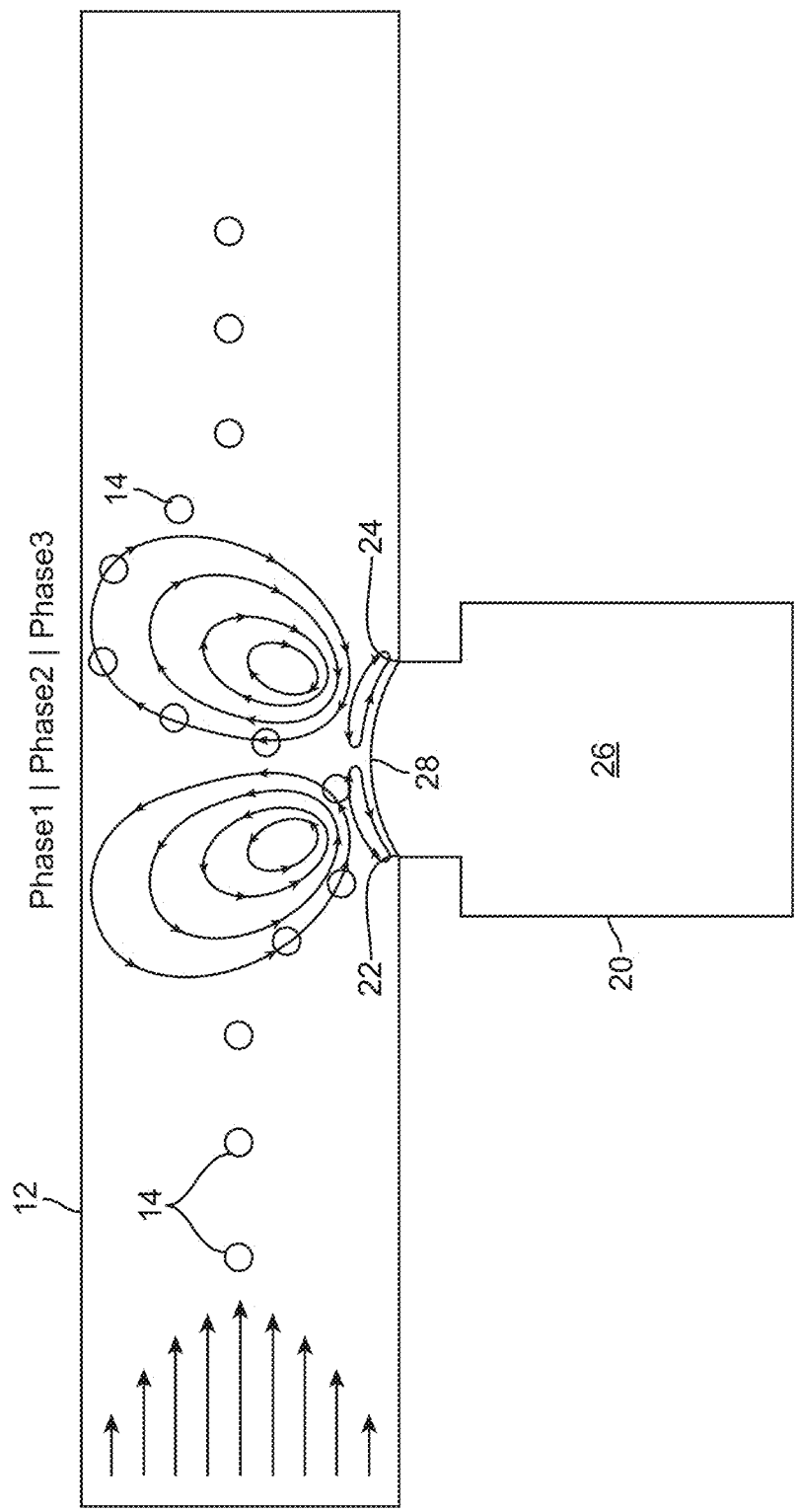
FIG. 1B illustrates streamlines of bulk flow with particles within a microchannel having an activated LCAT. Three different phases of micro-streaming flow are illustrated.

FIG. 1B illustrates the streamlines formed adjacent to the dead-end side channel 20 in response to actuation. When the microfluidic switching device 10 is not activated, the particles 14 will flow along the streamlines of the bulk flow. As a result particles 14 will not be displaced in the direction perpendicular to bulk flow. When the microfluidic switching device 10 is activated and bulk flow is present particles 14 are transported from the from the upstream microfluidic channel 12 to the outlet channels 16. As the particles 14 flow past the activated microfluidic switching device 10, they will be exposed to different phases of the micro-streaming flow. Three such phases are illustrated in FIG. 1B. The resulting drag force will initially pull the particle 14 towards the air-liquid interface (phase 1). As it flows through the center of the air-liquid interface, the acoustic micro-streaming flow will push the particles 14 away from the interface (phase 2). As the particles 14 pass the trailing edge 24 of the dead-end side channel 20 the particles 14 will be pulled towards the center of the channel (phase 3). The highest velocities of the micro-streaming occur at the center of the air-liquid interface 28. This results in the particle 14 having a maximum deflection during this phase (phase 2).

Figure 1C:
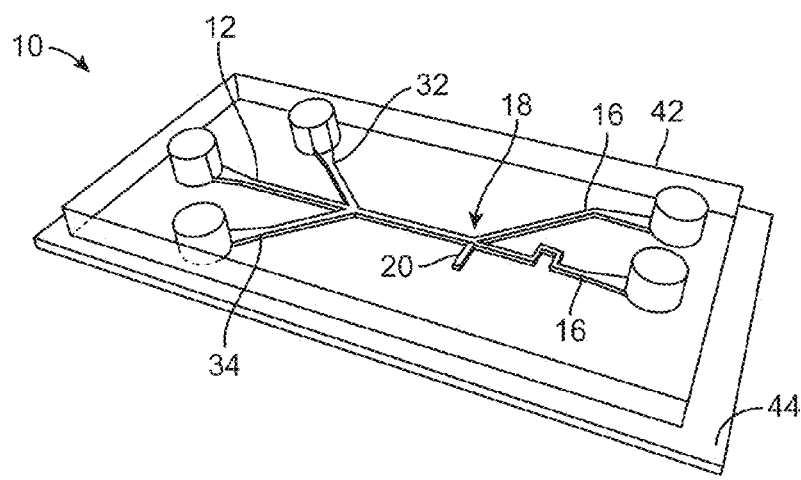
FIG. 1C illustrates a perspective view of another embodiment of a microfluidic switching device.
Figure 1D:
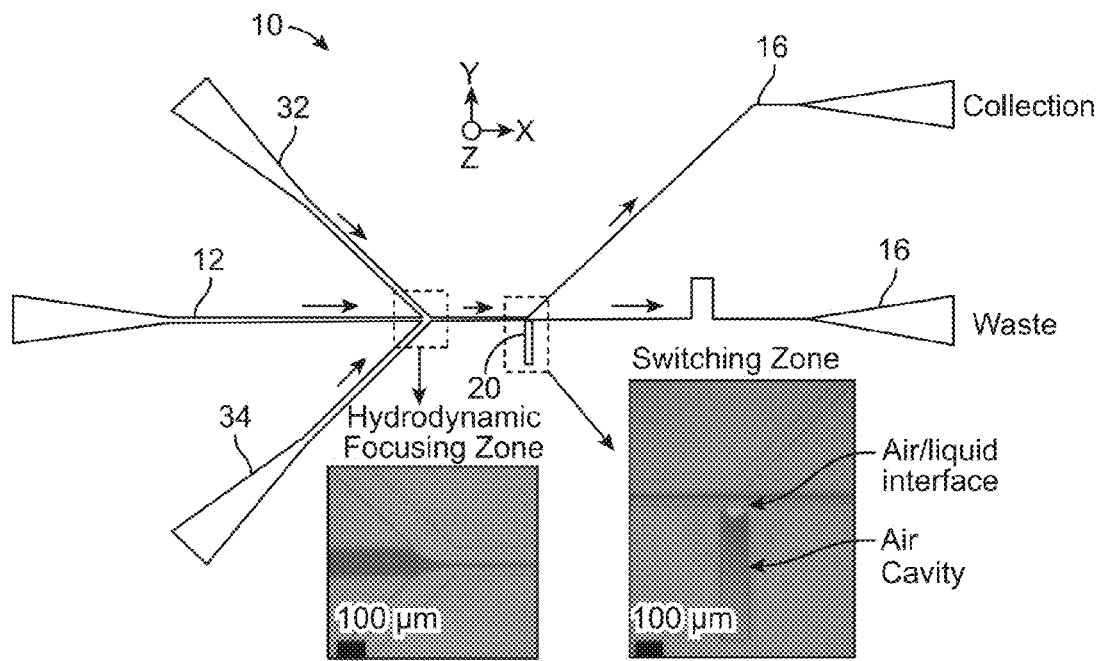
FIG. 1D illustrates a plan view of another embodiment of the microfluidic switching device of FIG. 1C.

FIGS. 1C and 1D illustrate another embodiment of a microfluidic switching device 10. In this embodiment, separate sheath flows 32, 34 are used to hydrodynamically focus flow within the upstream microfluidic channel 12. As seen in FIG. 1C, the dead-end side channel 20 is located at a bifurcation junction 18 with one outlet channel 16 being the collection outlet (upper outlet channel 16) while the remaining outlet channel 16 acts as a waste outlet. The three inlet channels 12, 32, 34 enable asymmetrical hydrodynamic focusing of particles 14 as they flow through the core inlet. A bifurcating outlet channel geometry located at the trailing edge 24 of the dead-end side channel 20 (as seen in FIG. 1A) enables the switching of particles as they flow past the actuated dead-end side channel 20. When the device 10 is in the OFF state particles flow through to the waste channel (lower outlet channel 16). When the device 10 is in the ON state the particles 14 are deflected into the collection channel 16 (upper channel 16). FIG. 1D illustrates a top down view of the microfluidic switching device 10 along with inset photographic images of the hydrodynamic focusing zone and the switching zone. As stated above, the trailing edge 24 of the dean-end side channel 20 is aligned with the bifurcation 18.

Figure 1E:
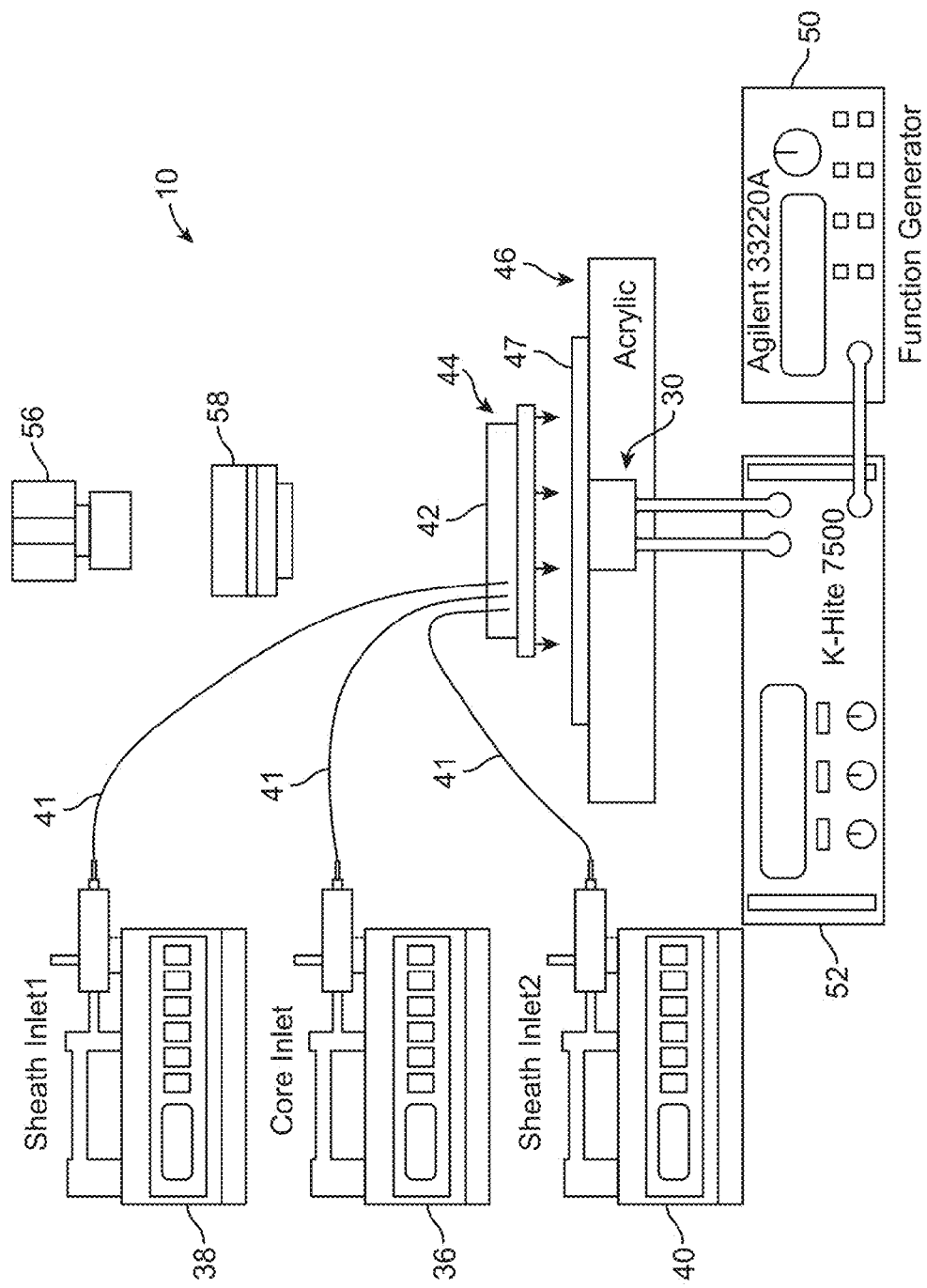
FIG. 1E illustrates a system containing the microfluidic switching device of FIG. 1C.

FIG. 1E illustrates another view of the microfluidic switching device 10 of FIGS. 1C and 1D along with various other components. As seen in FIG. 1E, a first syringe pump 36 is connected to the core channel/upstream microfluidic channel 12 via tubing 41. Second and third syringe pumps 38, 40 are connected, respectively to sheath inlet channels 32, 34 via tubing 41. As seen in FIG. 1D, the microfluidic switching device 10 is formed in a Polydimethylsiloxane (PDMS) substrate 42 that is bonded to a glass substrate 44. The combined structure is then secured to a platform 46 containing a transducer 30 therein. The platform 46 illustrated in FIG. 1D is an acrylic platform having a PZT transducer 30 contained therein. An acoustic coupling layer 47 as applied between the platform 46 and the glass substrate 44 (e.g., 350 μm). A function generator 50 is coupled to a voltage amplifier 52 that is connected to the transducer 30. The function generator 50, together with the voltage amplifier 52, applies an alternating current to the transducer 30. While the voltage may vary, the applied peak-to-peak voltage is typically less than about 25 $V_{pp}$.

Still referring to FIG. 1E, optionally, a camera 56 or other imager is provided along with a lens 58 such that the switching can be observed. The camera 56 is used, for example, during experiments described below. The camera 56 may also be used, however, as part of an imaging system to count or identify switched particles 14 that are collected in the outlet channel 16. The device 10 of FIGS. 1A-1E may be operated in either a continuous sorting mode whereby particles 14 are continuously sorted. Alternatively, the device 10 may be operated in a burst mode whereby a small subset or even a single particle 14 is sorted into an outlet channel 16.

Figure 2A:
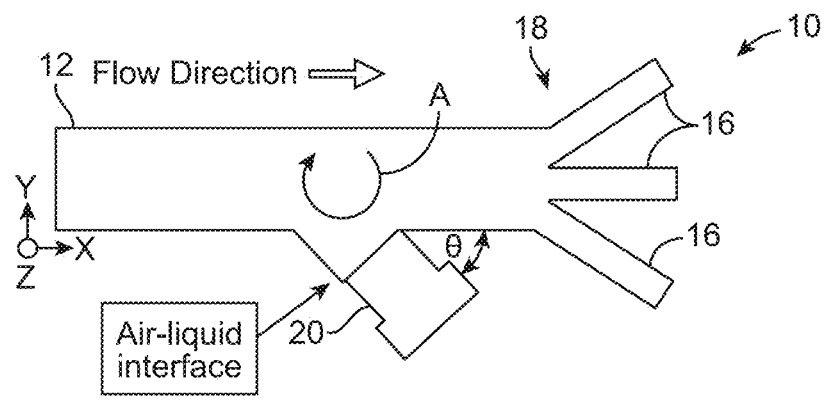
FIGS. 2A-2C illustrate different embodiments of microfluidic switching device.
Figure 2B:
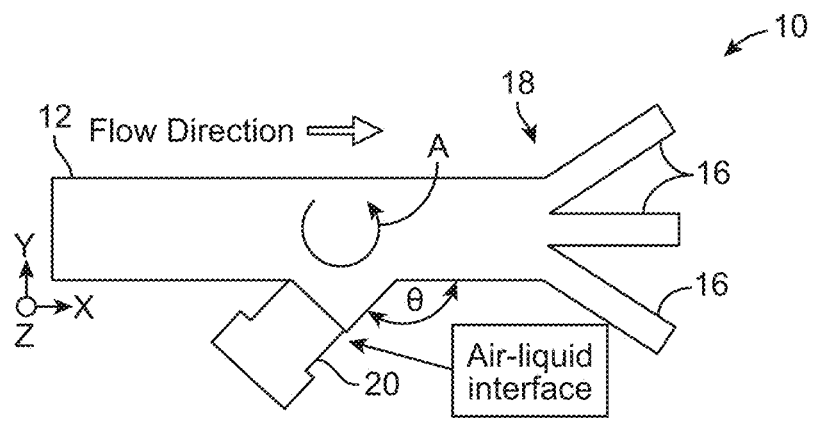

FIGS. 2A and 2B illustrate additional embodiments of a microfluidic switching device 10. In this embodiment, there is an upstream microfluidic channel 12 that terminates at a junction 18 with at least three outlet channels 16. In this embodiment, instead of having a dead-end side channel oriented generally perpendicular at the junction, a dead-end side channel 20 is provided that is angled with respect to axis of the upstream microfluidic channel 12. The angle θ may either be acute (FIG. 2A) or obtuse (FIG. 2B) with each orientation producing a single vortex with either a clockwise or counter-clockwise rotation as illustrated by arrows A. While three outlet channels are illustrated in FIGS. 2A and 2B it should be understood that the number of outlet channels 16 may be larger than three. While a single vortex is created, it is nonetheless stable.

Figure 2C:
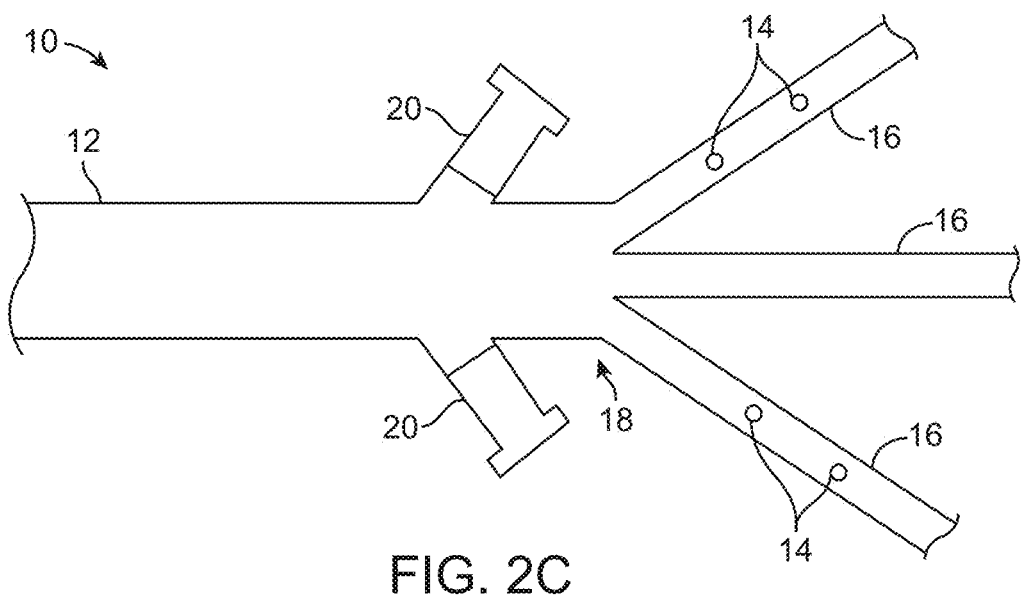

FIG. 2C illustrates still another embodiment of a microfluidic switching device 10. In this embodiment, a single microfluidic switching device 10 has multiple dead-end side channels 20 that are angled with respect to the upstream microfluidic channel 12. In this embodiment, the different vortices can be coupled to produce an additive or negative effect to push or pull particles 14 laterally across the upstream microfluidic channel 12 to direct the same into one of the plurality of outlet channels 16.

The microfluidic devices 10 can be fabricated using standard soft-lithography techniques, conventional polymer (e.g., plastic) fabrication techniques, hot embossing, or molding techniques. With respect to soft-lithography fabrication, the devices 10 include polydimethylsiloxane (PDMS) as the top substrate 42 and a 150 μm thick glass coverslip as the bottom substrate 44. The PDMS top substrate 42 (Sylgard 184, Dow Corning Corp., USA) having the various microchannels (i.e., upstream microfluidic channel 12 and outlets 16) are molded from an SU-8 master fabricated on a 3" silicon wafer. SU-8 50 (Microchem Corp., USA) is spun coated according to manufacturer's recommendations to obtain a photoresist layer thickness of ~50 μm on the wafer. This is exposed using a UV flood lamp through a transparency mask to produce the desired microchannel patterns after development using SU-8 developer (Microchem Corp., USA). A 10:1 ratio of PDMS base to curing agent is completely mixed, degassed and poured onto the SU-8 master and cured at 60° C. for four hours. The devices 10 are cut and plasma bonded to glass microscope coverslips after a 2 minute 30 second air plasma treatment of the surfaces at 250 mtorr. Upon bonding, the devices 10 are allowed to sit at room temperature for ten minutes to increase the bond strength between the PDMS and glass substrates. Rain-X (SOPUS Products, USA) is flowed through the device and allowed to incubate at room temperature for 10 minutes before being vacuumed out to form a hydrophobic coating on the walls of the microchannels. These devices 10 are then placed in a 120° C. oven for ten minutes and are then allowed to sit at room temperature for at least 24 hours before being used for experimentation.

LCAT devices exploit the phenomenon of acoustic microstreaming to manipulate fluid flow and suspended cells/particles within a microfluidic environment. Bubble-induced acoustic micro-streaming develops when bubbles trapped within a liquid phase oscillate when excited by a sound field. The oscillatory motion of the air-liquid interface leads to a first-order periodic flow within the liquid, with the period being the angular frequency of the applied sound field. At the bubble boundary the magnitude of the acoustic-excited flow is at a maximum and is given by $$u_b \sim d\omega \quad (1)$$

where d is the oscillation amplitude of the interface and ω is the angular frequency of the acoustic field. Within the oscillatory boundary layer, the first-order periodic flow induces a steady second-order streaming due to the balance between the viscous forces and the nonlinear inertial forces (i.e., Reynolds stresses) at the interface. The thickness of the oscillatory boundary layer δ, is described by $$\delta \sim (\nu/\omega)^{1/2} \quad (2)$$

where ν is the kinematic viscosity of the fluid. The magnitude of the steady micro-streaming within the oscillatory boundary layer is:

$$u_s \sim u_b^2/\omega R \quad (3)$$

where $u_s$ is the velocity of the streaming within the boundary layer and R is the radius of the oscillating bubble. For the frequencies used in the experiments described herein, the thickness of the boundary layer is on the order of several micrometers. However, the slip-conditions between the edge of the oscillatory boundary and the bulk fluid drives a steady vortex like streaming well beyond the edge of the boundary layer. The second-order streaming flows within the bulk fluid are utilized to switch cells and particles.

In order to better characterize particle trajectories induced by actuated LCAT-based devices, three-dimensional CFD simulations were conducted using the software package CFD-ACE+ v2008 (ESI Group, Inc., France). The simulation was set up using fluid flow and particle spray modules on a straight microchannel of dimensions 100 μm wide, 50 μm thick and 700 μm long with a structured grid of 10 μm³ throughout. The oscillatory air-liquid interface of an actuated LCAT device was modeled as an inlet with a time varying velocity profile described by the following equation:

$$v = \omega d \cos(x\pi/w)\sin(z\pi/l)\cos(\omega t) \quad (4)$$

This profile was used because it models the first degree motion of a rectangular membrane of dimensions w=60 μm and l=50 μm. The frequency of oscillation was 32 kHz and the peak to peak amplitude of the membrane (d) was set to 12 μm at the center. Membrane amplitude was set to 12 μm because it was observed visually that for an applied voltage of 20$V_{pp}$ membrane amplitude varied from ~10-12 μm. The total bulk flow rate in the microchannel was set to 5 μL/min at the inlet and the pressure at the outlet was set to the reference pressure of 100 kPa. A no-slip boundary condition was applied to all the walls within the microchannel. Seven 10 μm polystyrene beads were placed at the center of the channel along the z-axis approximately 120 μm upstream of the dead-end side channel.

The simulation was solved using constant time steps of 2 μsec which results in approximately 16 time steps per period of the air-liquid interface oscillation. Forces due to gravity were considered negligible and the reference pressure and temperature were set at 100 kPa and 300 K respectively. Forces due to drag were included in the spray module with the drag coefficient set to incompressible. The inlets were treated as walls with the coefficient of restitution (COR) set to 0.05 for the normal and 1.0 for the parallel components of the particle velocity upon collision with a microchannel wall. Initial velocity of all the fluid in the microchannel was set to 1×10⁻⁹ msec. The maximum iterations per time step were set to 40 with a convergence criterion of 0.0001 and a minimum residual of 1×10⁻¹⁸. An upwind spatial differencing method was used for velocity and the inertial relaxation for velocity was set to 0.2, while the linear relaxation was set to 1 for pressure, density and viscosity. The simulation was run for ~22 msec, in which all particles have flowed past the actuated dead-end side channel and towards the outlet. Property of water at 300K was used for the simulations with a dynamic viscosity of $\mu=8.55\times10^4$ kg m$^{-1}$ sec$^{-1}$ and density of $\rho=997$ kg m$^{-3}$.

Figure 3:
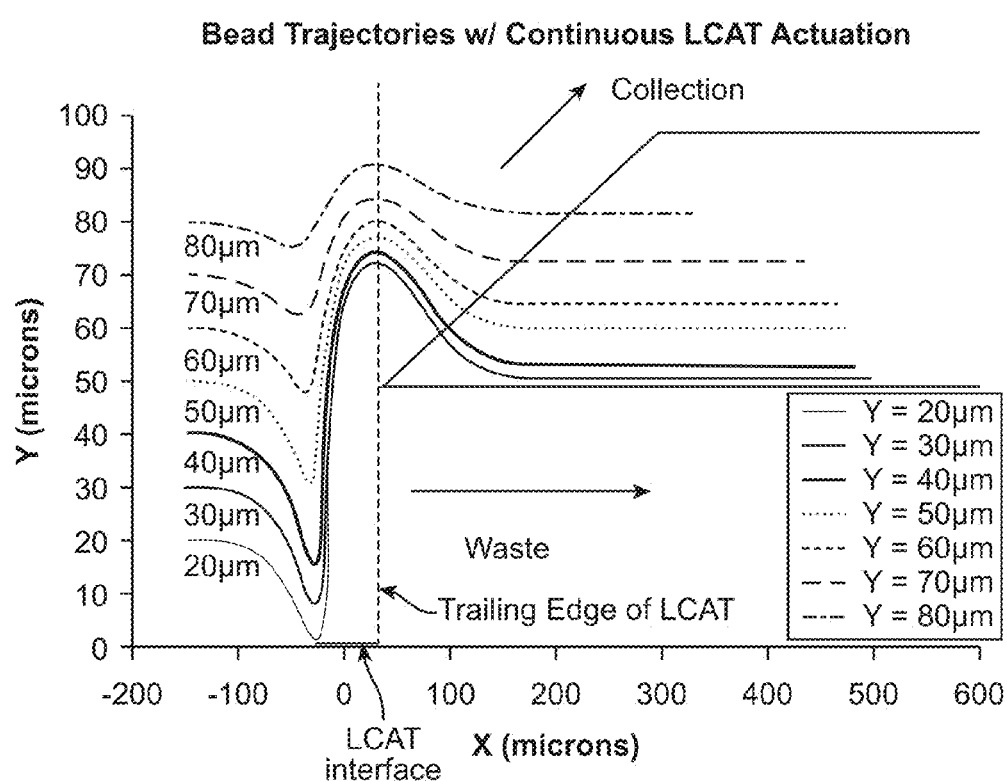
FIG. 3 illustrates a simulation graph showing particle path lines in the y direction (width of channel). X direction is the direction along the length of the microchannel. Z direction is out of plane of page.

The 10 μm polystyrene particle path lines from simulations conducted on a straight microchannel with a continuously activated dead-end side channel (LCAT feature) are shown in FIG. 3. Specifically, three distinct phases of particle deflection are observed. Initially as the particles flow towards the actuated dead-end side channel, all are pulled towards the air-liquid interface. In the second phase, as the particles flow between the front and back edge of the interface they are pushed away from the cavity due to the direction of micro-streaming flow. As they flow past the back edge of the dead-end side channel the particles are again pulled towards the center of the microchannel due to the direction of the streaming in that phase. Furthermore, particles closest to the dead-end side channel had the largest deflection in the order of ~50 μm, while particles furthest from the dead-end side channel had the smallest deflection of ~10 μm. The simulation demonstrates that an actuated dead-end side channel is capable of deflecting all particles in the direction perpendicular to the flow and that the magnitude of the deflection decreases as the initial distance between the air-liquid interface and the particle increases. As described above, the maximum deflection of all particles occurs at x=30 μm, the position where the back edge of the air-liquid interface is located along the x-axis (marked by the dashed line in FIG. 3). Therefore, a microfluidic device designed to have a symmetric bifurcation at the back edge of the dead-end side channel (shown in grey in FIG. 3) would enable the switching of particles and cells effectively. Symmetrical bifurcating outlet channels would require an asymmetrical particle flow focusing scheme which allows all particles to flow into the waste channel when the dead-end side channel is not actuated. However, when the dead-end side channel is actuated all particles will flow towards the collection channel due to their deflection away from the air-liquid interface.

Experimental

Experiments were conducted using the device 10 illustrated in FIGS. 1C-1E to switch particles (both beads and cells) into bifurcating microchannels. The platform that interfaces the piezoelectric transducer to the microfluidic device is illustrated in FIG. 1E and includes a 7 cm×7 cm×1 cm acrylic piece with an 11 mm hole drilled in its center. A 10 mm piezoelectric transducer (SMATR10H40×80, Steiner and Martins, Inc., USA) is inserted into the center and a thin layer of PDMS (~350 μm thick) is poured on to the top of the platform and allowed to cure at room temperature for 24 hours. The PDMS-based switch device (PDMS layer plus glass substrate) is placed on the platform and acoustically couples with the piezoelectric transducer due to the reversible bond between the bottom substrate of the device (glass coverslip) and the thin layer of PDMS on the platform.

Sheath fluid inlets 1 and 2 are used to asymmetrically focus the core fluid (suspension of particles/cells) ensuring that particles/cells flow into the waste outlet channel when the device is not actuated. The flow rates used for all experiments are 3 μL/min for sheath fluid 1, 1.2 μL/min for sheath fluid 2 and 0.8 μL/min for the core fluid and were controlled by syringe pumps (PicoPlus, Harvard Apparatus, USA). The piezoelectric transducer is supplied with a 32 kHz sinusoidal signal from a function generator (Agilent 33220A, Agilent Technologies, USA) and voltage amplifier (Krohn-Hite 7500, Krohn-Hite Corp., USA) with voltages ranging from 20-27 $V_{pp}$. The actuated transducer will cause the air-liquid interface of the LCAT to oscillate resulting in acoustic micro-streaming within the microchannel.

The device was characterized in order to determine the region around the dead-end side channel (LCAT) where a particle would be switched to the collection outlet when the LCAT is actuated. This region is referred to as the switching zone of the LCAT. In order to characterize the switching zone water was used as sheath fluid 1 at 3 μL/min and sheath fluid 2 at 1.2 μL/min, while 10 μm polystyrene beads (SPI Supplies, Inc., USA) suspended in a sucrose/deionized water solution of density 1.052 g/mL was flowed through the core inlet at 0.8 μL/min. The LCAT was actuated with two different sets of actuation times (1) ~3.1 msec of ON time and ~3.1 msec of OFF time and (2) ~1.6 msec of ON time and ~4.7 msec of OFF time) with a 32 kHz sine wave and a voltage of 20 $V_{pp}$. An LCAT ON time of 3.1 msec was chosen as it allows particles with the largest velocity (twice the average velocity) to be exposed to multiple phases of micro-streaming flow. While an LCAT ON time of 1.6 msec was chosen as it allows particles with the largest velocity to be exposed to a single phase of micro-streaming flow. A high speed camera (Phantom v310, Vision Research Inc., USA) captured images at 5000 fps with a 19 μsec exposure time. Switching zones were determined by analyzing the videos frame by frame. The velocity and position of each particle relative to the LCAT was calculated using ImageJ (NIH Image) particle analyzer function.

In order to determine if the LCAT device platform is capable of switching cells, K562 leukemia cells were flowed through the device and their viability was quantified using Trypan blue exclusion assay. First, K562 cells were spun down at 1000 rpm for 5 minutes and resuspended in culture media at a density of ~9-13×10$^6$ cells/mL. Phosphate buffered saline (PBS) was used as the sheath fluid at a flow rate of 3 μL/min (Sheath fluid 1) and 1.2 μL/min (Sheath fluid 2), while the cell suspension flow rate was 0.8 μl/min (Core fluid). LCAT was actuated for a 1 sec ON time and a 1 sec OFF time with a 32 kHz sine wave and a voltage ranging from 23$V_{pp}$-27$V_{pp}$. The device was allowed to switch cells for at least 1 hour while a high speed camera was used to monitor the device to ensure proper function. Cells were allowed to accumulate in wells punched out at the collection and waste outlets. Cells from the collection and waste wells along with a control (cells not flowed through the device) were spun down at 1000 rpm for 5 minutes and resuspended into ~30 μL of PBS. An equal volume of 0.4% Trypan blue was mixed with the cell suspension and allowed to incubate at room temperature for 5 minutes. Cells were counted using a hemocytometer to determine cell viability.

Figure 4A:
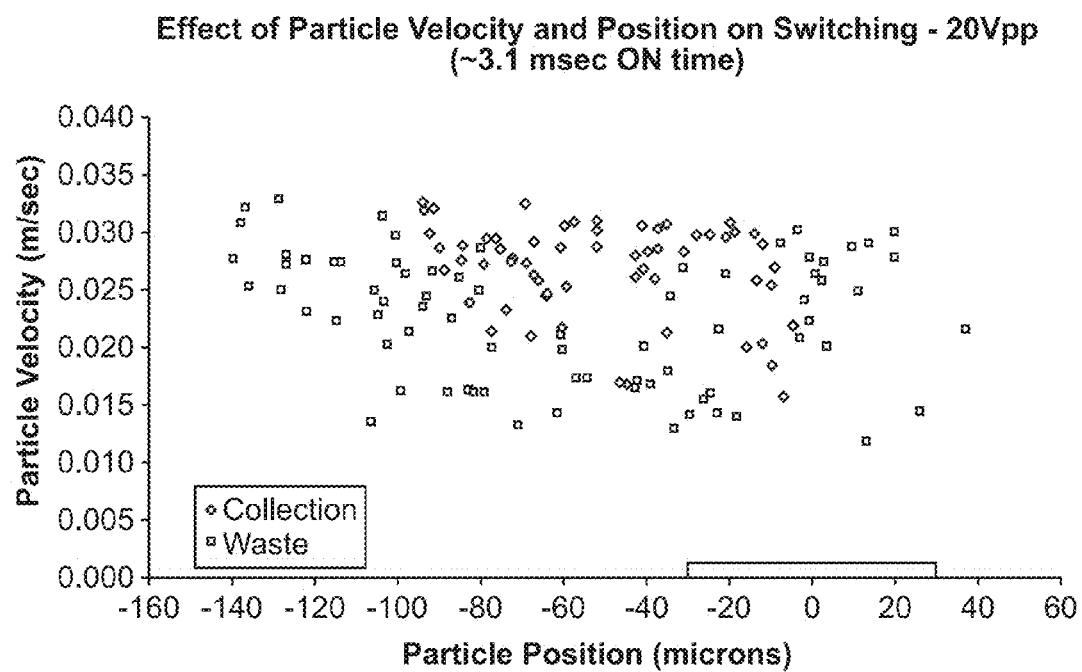
FIG. 4A illustrates a scatter plot showing the LCAT switching zone for 10 μm polystyrene particles for an LCAT ON time of 3.1 msec.
Figure 4B:
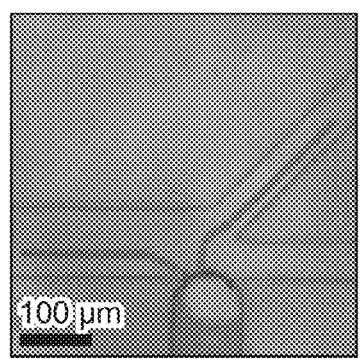
FIG. 4B illustrates a micrograph image of the LCAT switching zone for particles that were initially farther away from the LCAT.
Figure 4C:
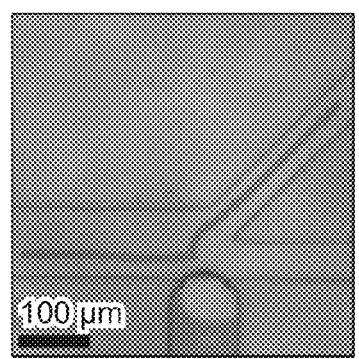
FIG. 4C illustrates a micrograph image of the LCAT switching zone for particles that were initially closer to the LCAT.

FIG. 4A illustrates a scatter plot showing the LCAT switching zone for 10 μm polystyrene particles for an LCAT ON time of 3.1 msec. Particles were analyzed frame by frame to determine their starting position relative to the LCAT and their initial velocity prior to LCAT actuation. The bar 100 on the x-axis of the plot indicates the location of the LCAT. It was observed that particles are switched to the collection channel within a narrow region of −15 μm<X<−6 μm independent of their initial velocity (X represents the center of the air-liquid interface created at the dead-end side channel). However for particles with initial position less than −15 μm it is greatly dependent on velocity. This is due to the fact that the residence time of the slower particles in regions of maximum micro-streaming is not long enough while the LCAT is in the ON state. Respective micrographs are illustrated in FIGS. 4B and 4C and show typical path lines observed for particles that were initially further away from the LCAT (FIG. 4B) and closer to the LCAT (FIG. 4C).

As shown in FIG. 4A there is a finite window in which particles affected by the LCAT will be switched to the collection channel. The switching zone is at its widest (~100 µm) for particles whose initial velocity is greater than 25 mm/sec. Particles whose position was within the range of −15 µm<x<−6 µm prior to the start of LCAT actuation were deflected to the collection channel independent of their initial velocity. However, for particles whose initial position to the left of −15 µm, only those with higher velocities were switched.

Figure 5A:
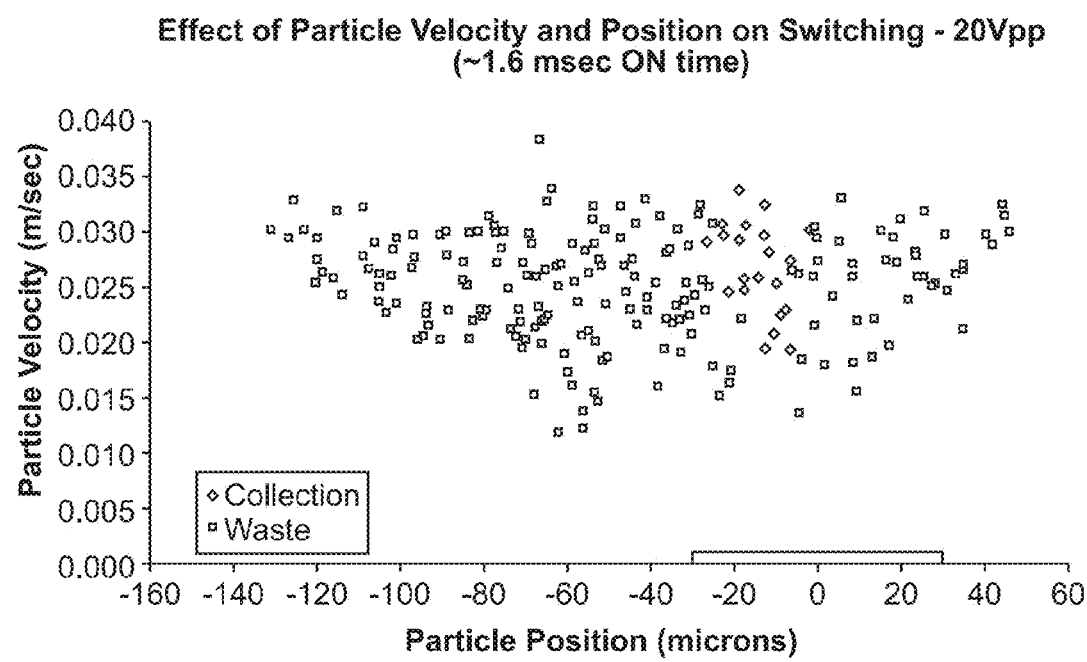
FIG. 5A illustrates a scatter plot showing the LCAT switching zone for 10 um polystyrene particles for an LCAT ON time of ~1.6 msec.
Figure 5B:
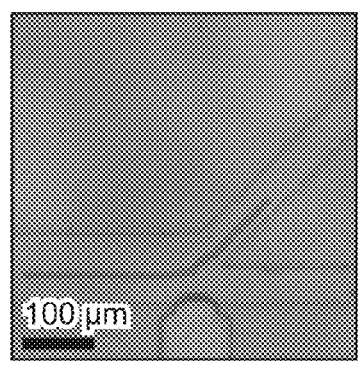
FIG. 5B illustrates a micrograph that shows the typical path line observed for particles switched with a LCAT ON time of ~1.6 msec.

FIG. 5A illustrates the same scatter plot showing the LCAT switching zone for 10 um polystyrene particles for an LCAT ON time of ~1.6 msec. Particles that are within the region indicated in switching zone of FIG. 1D were analyzed to determine their position relative to the LCAT and their initial velocity prior to LCAT actuation. The bar on the x-axis of the plot indicates the location of the LCAT. It was observed that the switching zone for an LCAT ON time of ~1.6 msec was reduced to 20 um, 20% of that observed for an ON time of ~3.1 msec. Although particles outside of the 20 um range were deflected, the deflection was not significant enough to cause actual switching. With a narrower switching zone, the inter-particle spacing required to obtain high purity can be reduced, thus increasing the throughput of an LCAT cell/particle switch. A micrograph is illustrated in FIG. 5B shows the typical path line observed for particles switched with an LCAT ON time of ~1.6 msec.

It is important to note that the initial velocity of particle within the 20 µm switching zone does not significantly determine whether it is switched to the collection channel. The different initial velocities indicate that the particle is flowing through the microchannel along different positions on the z-axis. Since particle velocity does not determine whether it is switched to the collection channel, three-dimensional particle focusing is not required to ensure that the particles are within the center of the microchannel along the z-axis. This will greatly reduce the complexity of a microfluidic sorting platform based on the LCAT switch.

Taking into consideration the average velocity of particles flowing through the microchannel for a 5 µL/min flow rate used in the experiments conducted (~17 mm/sec) and the minimum required inter-particle distance of 20 µm (based on the width of the switching zone) the calculated theoretical switching rate of the system should be ~800 particles/sec. Further increase in the flowrate, optimization of the voltage applied to the PZT as well as the LCAT ON time will allow for faster switching rates resulting in an increased throughput of an LCAT based sorting platform. For example, doubling the flow rate to 10 µL/min will result in an average velocity of particles to be ~34 mm/sec. The residence time of the particles within the switching zone will decrease by half, therefore a higher actuation voltage will be required in order to deflect the particle to the collection outlet. However, if the width of the switching zone is maintained at 20 µm then the theoretical switching rate should be ~1,600 particles/sec.

It should be understood that the LCAT based switch device may also be used to switch particles at substantially lower switching rates. For example, certain applications may not require high switching rates. The LCAT based switch device may still be used even at switching rates substantially below 800 particles/second. In some cases, the switching rate may be tunable.

Although the LCAT based switch device was characterized using 10 µm polystyrene beads in order to determine its switching zone, it was also determined if an LCAT switch would be capable of switching cells. K562 cells were flowed through the device and switched into the collection and waste outlets as described in the previous section. With the LCAT in the ON state for 1 second, cells were observed to flow into the collection outlet, while with the LCAT in the OFF state, cells flowed into the waste outlet. Cells in the collection well were exposed to the micro-streaming induced by the LCAT while cells in the waste well were not. The Trypan blue exclusion assay results are shown in Table 1 below. Multiple switching experiments were conducted (n=3) with each experiment lasting more than 1 hour. Trypan blue exclusion assays were performed using a hemocytometer on cells collected from collection, waste and control (cells not flowed through the device) populations. For each experiment conducted, at least 300 cells were counted from each population.

TABLE 1

| | Cell Viability (%) |
|---|---|
| Collection | 94.5 ± 4.7 |
| Waste | 96.2 ± 0.5 |
| Control | 97.8 ± 2.1 |

Although cell viability in both collection and waste channels were slightly lower than those of the control, an average cell viability of 94% was obtained, which is comparable to or exceeds previously reported values for cell viabilities for other microfluidic cell switches. This indicates that an LCAT switch does not compromise the membrane of cells and can be utilized as an actuator for an integrated sorting platform.

While embodiments of the present invention have been shown and described, various modifications may be made without departing from the scope of the present invention. The invention, therefore, should not be limited, except to the following claims, and their equivalents.

What is claimed is:
1. A microfluidic switching device comprising:
an upstream microfluidic channel configured to contain a liquid having particles therein;
at least three outlet channels coupled to the upstream microfluidic channel at a junction;
a first dead-end side channel oriented at an angle with respect to the upstream microfluidic channel and coupled to the upstream microfluidic channel at the junction, the first dead-end side channel having a gas contained therein;
a second dead-end side channel located on an opposing side of the upstream microfluidic channel as the first dead-end side channel, the second dead-end channel oriented at an angle with respect to the upstream microfluidic channel and coupled to the upstream microfluidic channel at the junction, the second dead-end side channel having a gas contained therein;
a transducer, wherein actuation of the transducer moves the particles laterally across the upstream microfluidic channel into one of the at least three outlet channels; and
wherein the upstream microfluidic channel, the at least three outlet channels, the first dead-end side channel, and the second dead-end side channel are formed in a polydimethylsiloxane (PDMS) substrate and the PDMS substrate is bonded to a glass substrate and the transducer is acoustically coupled to the glass substrate.

2. The microfluidic switching device of claim 1, wherein the upstream microfluidic channel is coupled to a first sheathing channel and a second sheathing channel at an upstream location.

3. The microfluidic switching device of claim 1, wherein the particles comprise cells.

4. The microfluidic switching device of claim 1, further comprising an imager configured to image one or more of the at least three outlet channels.

5. The microfluidic switching device of claim 1, wherein a switching rate of the microfluidic switching device is tunable.

6. The microfluidic switching device of claim 1, wherein the transducer is actuated in an on state for a period of time between about one millisecond and about four milliseconds.

7. The microfluidic switching device of claim 1, wherein the first dead-end side channel and the second dead-end side channel are oriented at an acute angle with respect to the upstream microfluidic channel.

8. The microfluidic switching device of claim 1, wherein the first dead-end side channel and the second dead-end side channel are oriented at an obtuse angle with respect to the upstream microfluidic channel.

9. The microfluidic switching device of claim 1, wherein the upstream microfluidic channel comprises a focusing zone.

* * * * *